(12) United States Patent
Amron

(10) Patent No.: US 7,905,674 B2
(45) Date of Patent: Mar. 15, 2011

(54) FOUNTAIN TOOTHBRUSH

(76) Inventor: Scott L. Amron, Westbury, NY (US)

( * ) Notice: Subject to any disclaimer, the term of this patent is extended or adjusted under 35 U.S.C. 154(b) by 0 days.

(21) Appl. No.: 12/605,956

(22) Filed: Oct. 26, 2009

(65) Prior Publication Data
US 2010/0107349 A1     May 6, 2010

Related U.S. Application Data (63) Continuation-in-part of application No. 11/821,353, filed on Jun. 22, 2007, now Pat. No. 7,607,851, which is a continuation-in-part of application No. 11/401,702, filed on Apr. 11, 2006, now abandoned.

(51) Int. Cl.
*A46B 11/00*      (2006.01)
(52) U.S. Cl. ............................ 401/268; 401/282; 401/289
(58) Field of Classification Search .................. 401/268, 401/270, 282–291; 15/106, 105, 159.1
See application file for complete search history.

(56) References Cited

U.S. PATENT DOCUMENTS

| | | | |
|---|---|---|---|
| 1,097,122 A | 5/1914 | Engstrom | |
| 2,028,519 A | 1/1936 | Peterkin et al. | |
| 2,548,255 A | 4/1951 | Cressler | |
| 3,593,707 A | 7/1971 | Pifer | |
| 3,610,234 A | 10/1971 | Oates | |
| 3,869,746 A | 3/1975 | Man-King | |
| 4,412,823 A | 11/1983 | Sakai et al. | |
| 4,582,075 A | 4/1986 | O'Neal et al. | |
| 5,231,978 A | 8/1993 | Kao et al. | |
| 5,746,595 A | 5/1998 | Ford | |
| 6,047,429 A | 4/2000 | Wu | |
| 6,233,773 B1 | 5/2001 | Karge et al. | |
| 6,357,072 B1 | 3/2002 | Zinn | |
| 6,689,078 B1 | 2/2004 | Rehkemper et al. | |

*Primary Examiner* — David J Walczak
(74) *Attorney, Agent, or Firm* — Cohen Pontani Lieberman & Pavane LLP

(57) ABSTRACT

A toothbrush body includes a handle connected to a head and bristles projecting from the top of the head. An open channel runs longitudinally along the body between a first open end and a second closed end such that the first open end is in communication with the second closed end through the open channel. The open channel, the first open end, and the second closed end are arranged so that a substantially downward running stream of water directed into the first open end is redirected through the channel and out of the closed second end to form a fountain. A direction of a flow of the fountain at the other of the first opening and the second opening has an upward component so that a user, i.e., holder of the toothbrush, can use the fountain for oral rinsing.

19 Claims, 7 Drawing Sheets

FOUNTAIN TOOTHBRUSH

CROSS REFERENCE TO RELATED APPLICATIONS

This application is a continuation-in-part of U.S. patent application Ser. No. 11/821,353, now U.S. Pat. No. 7,607,851, filed on Jun. 22, 2007, which is a continuation-in-part of U.S. patent application Ser. No. 11/401,702, filed on Apr. 11, 2006 now abandoned, the entirety of both references is incorporated herein by reference.

BACKGROUND OF THE INVENTION

The present invention relates to a toothbrush with a channel for redirecting at least a portion of a faucet stream.

Brushing teeth is an essential part of any oral hygiene routine. It is recommended that brushing be performed after every meal. However, if a person is not at home, a cup may not be readily available for rinsing after brushing.

Even if a cup is available, cups collect dirt and require frequent cleaning and may not be desirable for use. The use of paper cups solves this problem but is not environmentally friendly as it creates waste. Water directly from a faucet may be used for rinsing. However, it is difficult to get the water from the faucet to a user's mouth without a cup. It is difficult to get enough water using cupped hands. Furthermore, the use of cupped hands may create splashes and spillage. It is also awkward to reach the stream exiting the faucet directly. Accordingly, there is a need for a simple and sanitary means for oral rinsing after brushing.

SUMMARY OF THE INVENTION

An object of the invention is to provide a toothbrush that facilitates oral rinsing without the problems associated with the prior art.

The object is met by a toothbrush having a body with a handle portion connected to a head portion, the body having a top and a bottom, and bristles projecting from the top of said head portion. The body defines an open channel having a first open end and a second closed end such that said first end is in communication with said second end through said channel.

The channel and the first and second ends are arranged so that a substantially downward running stream of water directed into the first open end is redirected through the channel and out of the second closed end to form a fountain. A direction of a flow of the fountain at the second end has an upward component so that a user, i.e., holder of the toothbrush, can easily reach the fountain for oral rinsing.

According to one embodiment of the invention, a toothbrush includes a head portion having bristles projecting from said head portion and a body having a handle portion connected to the head portion. The body has a plurality of sides, and an open channel arranged on one of the plural sides. The open channel includes a first open end, a second closed end such that said first end is in communication with said second end through said open channel, a pair of side walls between the first open end and the second closed end, and a channel floor delimited by the open end, the closed end, and the side walls, wherein the pair of side walls extend from the channel floor at an angle of at least 90° and a depth of the channel increases from the first open end to the closed second end. The first open end and the second closed end are arranged so that at least a portion of a substantially downward running stream of water directed into said first open end is redirected through said open channel and out of the second closed end to form a fountain, thereby availing to a user of the toothbrush a supply of water for rinsing.

According to one embodiment of the invention, at least one of the first and second ends are arranged on the head portion.

According to one embodiment of the invention, both of the first and second ends are arranged on the head portion on a side of the head portion opposite the bristles.

According to one embodiment of the invention, the channel floor defines a bowl-shaped trough.

According to one embodiment of the invention, a width of the first end between the pair of walls is between 2 mm and 14 mm.

According to one embodiment of the invention, said width of the first end between the pair of walls is 4.5 mm.

According to one embodiment of the invention, the channel floor between the open end and the closed end is at least 10 mm.

According to one embodiment of the invention, the second closed end is substantially V-shaped.

According to one embodiment of the invention, the second closed end is substantially U-shaped.

According to one embodiment of the invention, a height of the pair of side walls at the second end is between about 2 mm and about 6 mm.

According to one embodiment of the invention, the height of the pair of side walls at the second end is about 4.5 mm.

According to one embodiment of the invention, the channel is integrally formed with at least one of the head portion and the body portion.

According to one embodiment of the invention, the channel is affixed to at least one of the head portion and the body portion.

According to one embodiment of the invention, each of the walls of the pair of side walls extends radially from the toothbrush body, each wall rising from the first open end to the second closed end at an angle of at least 5°.

According to one embodiment of the invention, the pair of side walls is arranged symmetrically with respect to a longitudinal axis of the toothbrush.

According to one embodiment of the invention, the side walls are arranged asymmetrically with respect to a longitudinal axis of the toothbrush.

According to one embodiment of the invention, the channel is arranged to form the fountain directed towards the head portion of the toothbrush.

According to one embodiment of the invention, the channel is arranged to form the fountain directed away from the head portion of the toothbrush.

According to one embodiment of the invention, the channel floor is substantially flat.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, wherein like reference characters denote similar elements throughout the several views:

FIGS. 8A-8K are different embodiments of the channel shown in perspective view;

DETAILED DESCRIPTION OF THE PRESENTLY PREFERRED EMBODIMENTS

Figure 1:
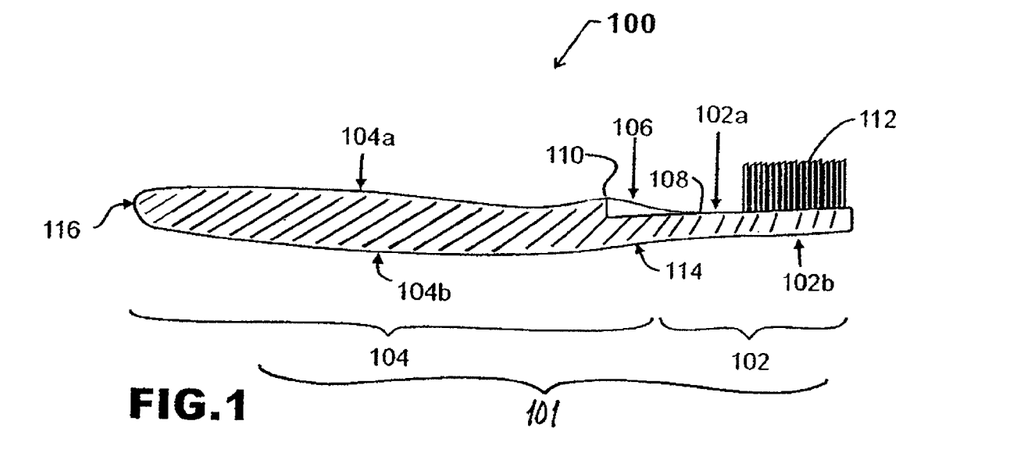
FIG. 1 is a longitudinal sectional view of a toothbrush according to an embodiment of the present invention.
Figure 3:
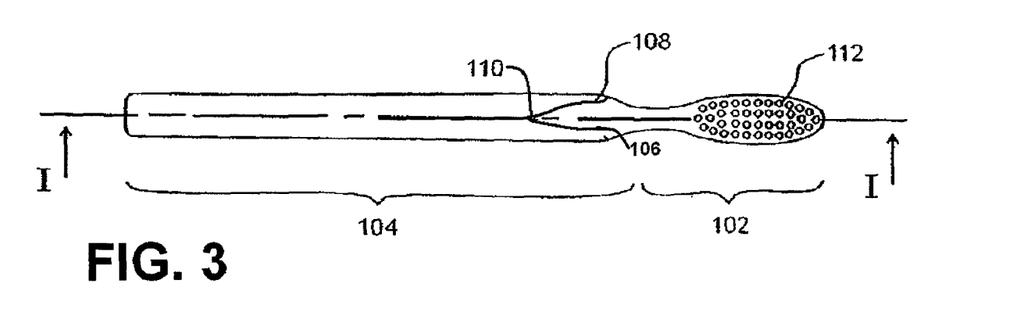
FIG. 3 is a plan view of the toothbrush of FIG. 1.

FIGS. 1 and 3 show a toothbrush 100 according to an embodiment of the present invention. The toothbrush has a body 101 including a handle 104 and a head 102. The handle 104 includes a top 104a and a bottom 104b. Likewise, the head 102 includes a top 102a and a bottom 102b. Bristles 112 are arranged on the top 102a of the head 102. While disclosed with respect to a manual toothbrush, an electric toothbrush can be implemented with the disclosed channel.

Figure 2:
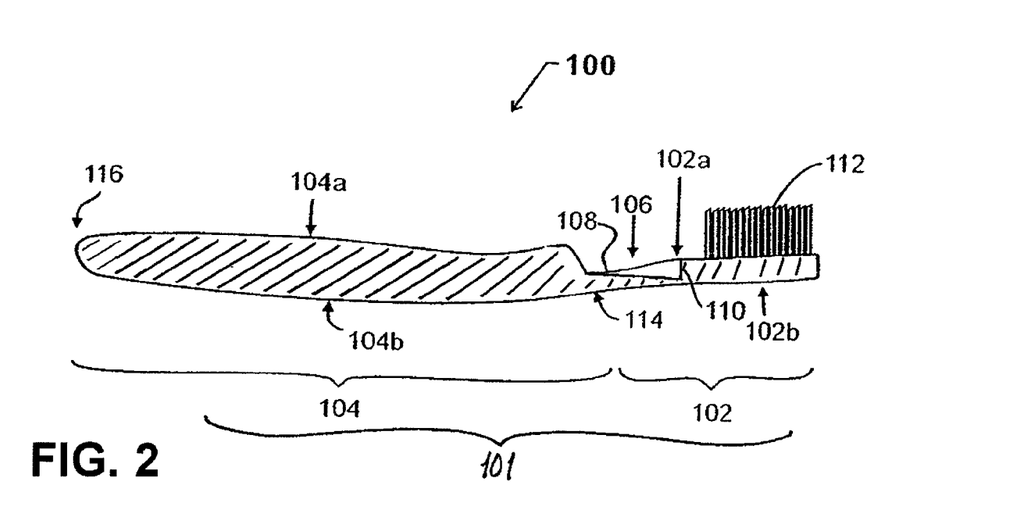
FIG. 2 is a longitudinal sectional view of a toothbrush according to an embodiment of the present invention.

The handle 104 has a first end 114 proximate the head 102 and a second end 116 arranged distally from the head 102. An open channel 106 extends longitudinally along the handle 104 between a first open end 108 and a second closed end 110. Both the first open end 108 and the second closed end 110 are arranged on the top 104a of the handle 104. The first open end 108 is arranged proximate to the head 102 and the second closed end 110 is arranged distally from the head 102. Alternatively, as shown in FIG. 2, the first open end 108 is arranged distally from the head 102 and the second closed end 110 is arranged proximate to the head 102. As shown in FIG. 1, the sidewalls that forms channel 108 extend at an angle from the first open end 108 to the second closed end 110. The sidewalls extend at an angle of at least 5°. It should be noted that the second closed and 110 forms an angle with a floor of the channel of at least 90°. While other angles can be used, including angles less than 90°, an angle of at least 90° is preferable for molding.

When a downward stream of water is presented to the toothbrush between the opening 108 and the bristles 112, the water stream splits so that a first portion of the stream enters channel 106, a second portion of the stream runs through bristles 112 rinsing the bristles 112, and the remainder of the stream passes down around the handle 104 and head 102. In a preferred embodiment, the stream is presented to the first open end 108 of channel 106. Alternatively, the stream is before the channel 106 in front of first open end 108.

Figure 4:
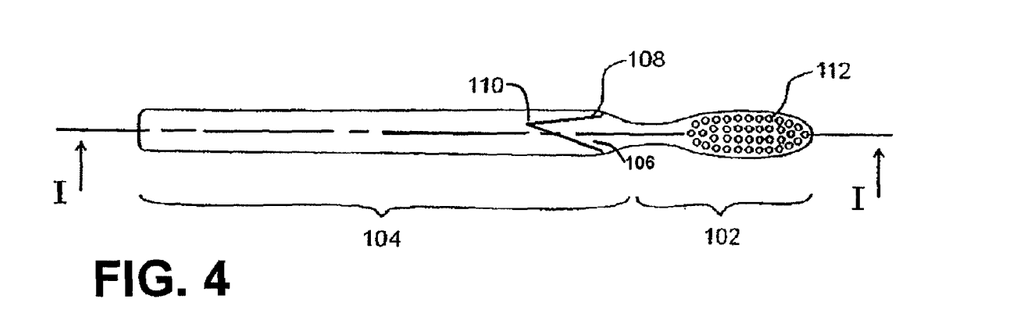
FIG. 4 is a plan view of the toothbrush of FIG. 1 according to an embodiment of the present invention.

As shown in FIG. 3, the walls that form channel 106 are arranged symmetrically with respect to a longitudinal axis of the toothbrush 100. Rotating the body about its longitudinal axis will direct the output in the direction of rotation. Alternatively, as shown in FIG. 4, the walls that form channel 106 are arranged asymmetrically with respect to a longitudinal axis of the toothbrush 100. The walls can be curved, either concave or convex, as shown in FIG. 3 or straight as shown in FIG. 4. In one embodiment, the open end 108 is narrower than a maximum channel width. Alternatively, the walls are substantially parallel, ending in a U-shape.

Figure 5:
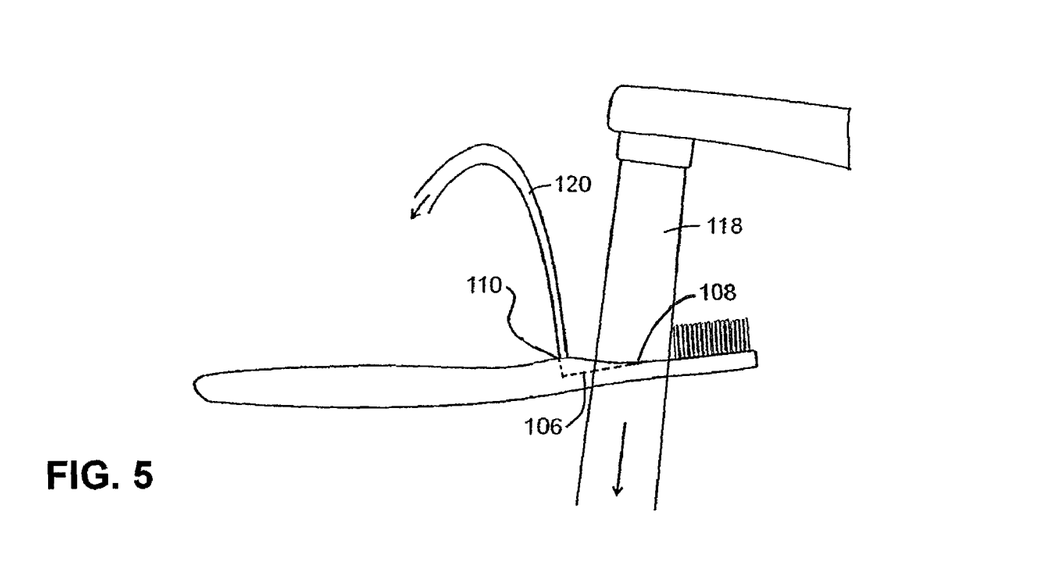
FIG. 5 is a side view of the toothbrush of FIGS. 1 and 2 held under a faucet.

As shown in FIG. 5 the first open end 108 is placed facing upstream in a water stream 118 flowing from a faucet. At least a portion of the water stream 118 enters the channel 106 through opening 108 and is redirected through the channel 106 to form a fountain 120 flowing out of the second closed end 110 in the top 104a of the handle 104. In a preferred embodiment, the water stream splits when it hits the opening 108. The opening 108 can be angled downward, i.e., head downward or substantially horizontal. A portion of the water then flows through the channel 106. As shown in FIG. 5, the fountain 120 is directed upwards and toward the second end 116 of the handle 104. The channel 106 and second closed end 110 may alternatively be arranged so that the fountain flows out of the second opening in a direction that is approximately perpendicular to the top 104a of the handle 104. The different arrangements of the channel 106 shown in FIGS. 2 and 4 will provide streams 120 directed away from the body 104 at different exit angles. While FIG. 5 shows the toothbrush substantially horizontal, the fountain effect occurs when the toothbrush is at an angle with respect to the horizontal, including a downward angle so that an upstream portion of stream 118 enters opening 108. Thus, in contrast to a scoop or cup-shape, the disclosed open channel 106 is configured to produce a fountain when oriented at any angle with respect to the water stream 118. For example, the stream 102 in FIG. 5 can be oriented in a downward direction and the fountain 120 is still produced.

In a preferred embodiment, the exit, closed end 110, is V-shaped or U-shaped. Preferably, closed end 110 has about a 2 mm diameter. The side walls are slightly rounded and converge inward toward closed end 110. The floor of channel 106 is substantially flat. However, in an alternative embodiment, the floor of channel 106 has a slight tubular indent to guide. In the preferred embodiment, the sidewalls of channel 106 rise from the open end 108 to the exit lip, second closed end 110 so the channel 106 is directional. Run-off is preferably guided down and away toward the head 102 of toothbrush 100 in an area where there are no side walls. The body of the toothbrush 100 preferably does not have a flat plateau at the top of the side walls forming channel 106. In a preferred embodiment, the side walls forming channel 106 curve to allow water to flow around the body of toothbrush 100.

The handle 104 of the toothbrush 100 in FIGS. 1 and 2 is preferably translucent, at least in the area of the channel 106, so that a user can detect the presence of any dirt, mold, or other obstruction in channel 106, and thus relieves any sanitary concerns that an otherwise reluctant user might have. Furthermore, the handle 104 may be made of a material that does not promote the growth of molds such as, for example, nylon. Mold requires some food to grow. Therefore, at least the portion of the toothbrush defining the channel is preferably made of nylon, TPE, or another material having a slick or non-sticking surface which allows food to easily wash off and thereby prevents mold growth. This is the preferred material for all embodiments of the channel described herein. Moreover, the arrangement of the channel along the longitudinal extent of the toothbrush allows any water in the channel to drip out when the toothbrush rests upright in a holder. In one embodiment, a portion of the channel walls is made of TPE to be softer for the user. Additionally, a softer material allows the shape of channel 106 to change under higher pressure streams to become more efficient and catch more water under the higher pressure stream.

The size of the first open end 108 and the second closed end 110 and the cross-section of the channel 106 must be small enough so that the overall size of the handle is small enough to fit in a toothbrush holder when the channel 106 is arranged at the end 116 of the handle 104, and must be large enough to supply a sufficient amount of water for oral rinsing. Furthermore, the first open end 108 is larger than the second closed end 110 to facilitate collection of water from the faucet stream 118 and increase the velocity of the water exiting the second closed end 110.

In a specific embodiment, the first open end 108 is between about 2 mm and about 14 mm wide. In a preferred embodiment, the first open end 108 is 6 mm wide. In a specific embodiment, the channel 106 is at least 15 mm long as measured longitudinally along the body of the toothbrush 100. In a preferred embodiment, the channel 106 is at least 20 mm long. In one embodiment, the second closed end 110 is V-shaped. In an alternative embodiment, the second closed end 110 is U-shaped. In a preferred embodiment, the second closed end has a diameter of about 2 mm.

Figure 6A:
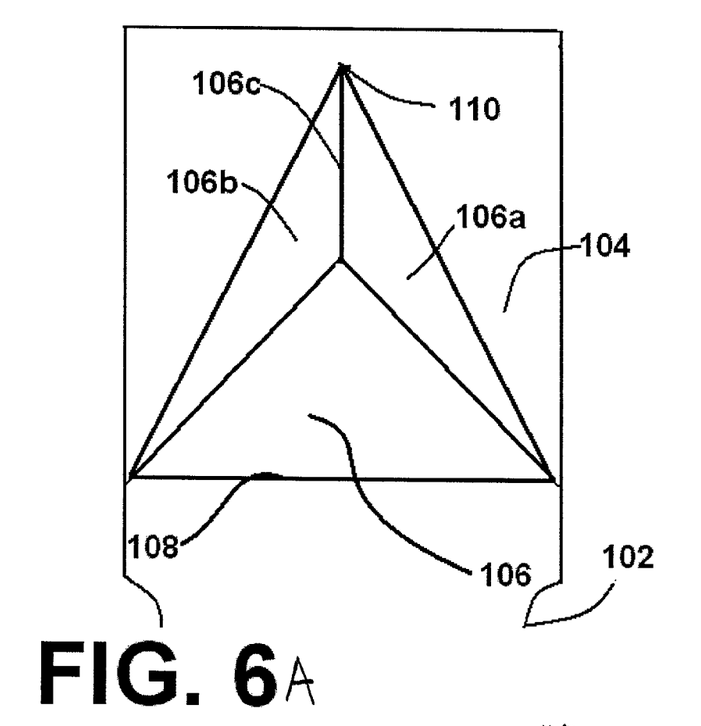
FIG. 6A is a partial perspective view of the toothbrush of FIGS. 1 and 3.

As shown in FIG. 6A, the channel 106 is formed by sidewalls 106a, 106b. The sidewalls meet at the second closed end 110 along a line 106c. The floor of the channel 106 is delimited by sidewalls 106a, 106b and the first open end 108. In a specific embodiment, a height of sidewalls 106a, 106b at the second closed end 110 represented by 106c is between about 2 mm and about 6 mm. In a preferred embodiment, a height of sidewalls 106a, 106b at the second closed end 110 represented by 106c is 4.5 mm.

Figure 6B:
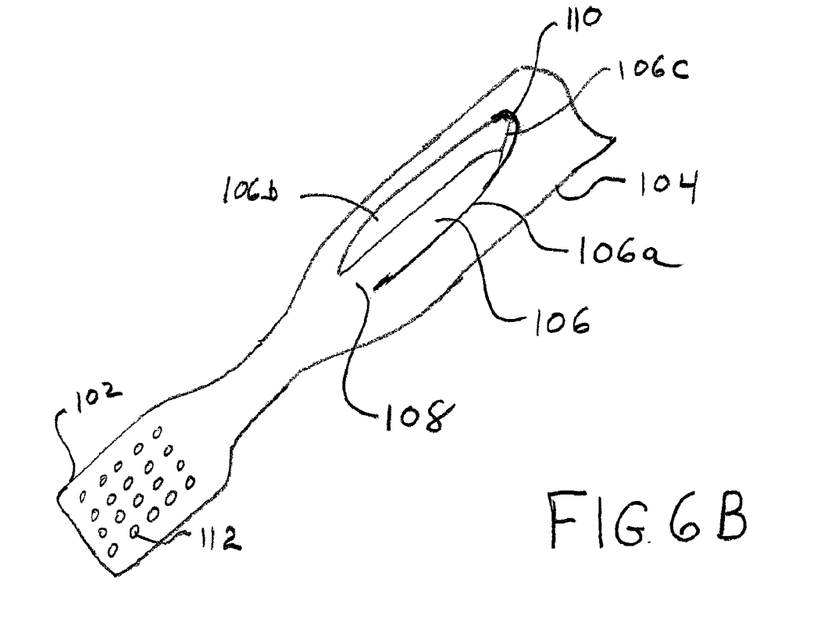
FIG. 6B is a partial perspective view of the toothbrush of FIGS. 1 and 3.

As shown in FIG. 6B, the channel 106 is formed by sidewalls 106a, 106b. The sidewalls meet at the second closed end 110 along a line 106c. The floor of the channel 106 is delimited by sidewalls 106a, 106b and the first open end 108. In a specific embodiment, the walls 106a and 106b meet at the floor in a V-shape and at the upper end of the walls, opposite the floor, the meeting is U shaped. Additionally, in a preferred embodiment, the walls bow out slightly from the floor to the top of the wall.

Figure 7:
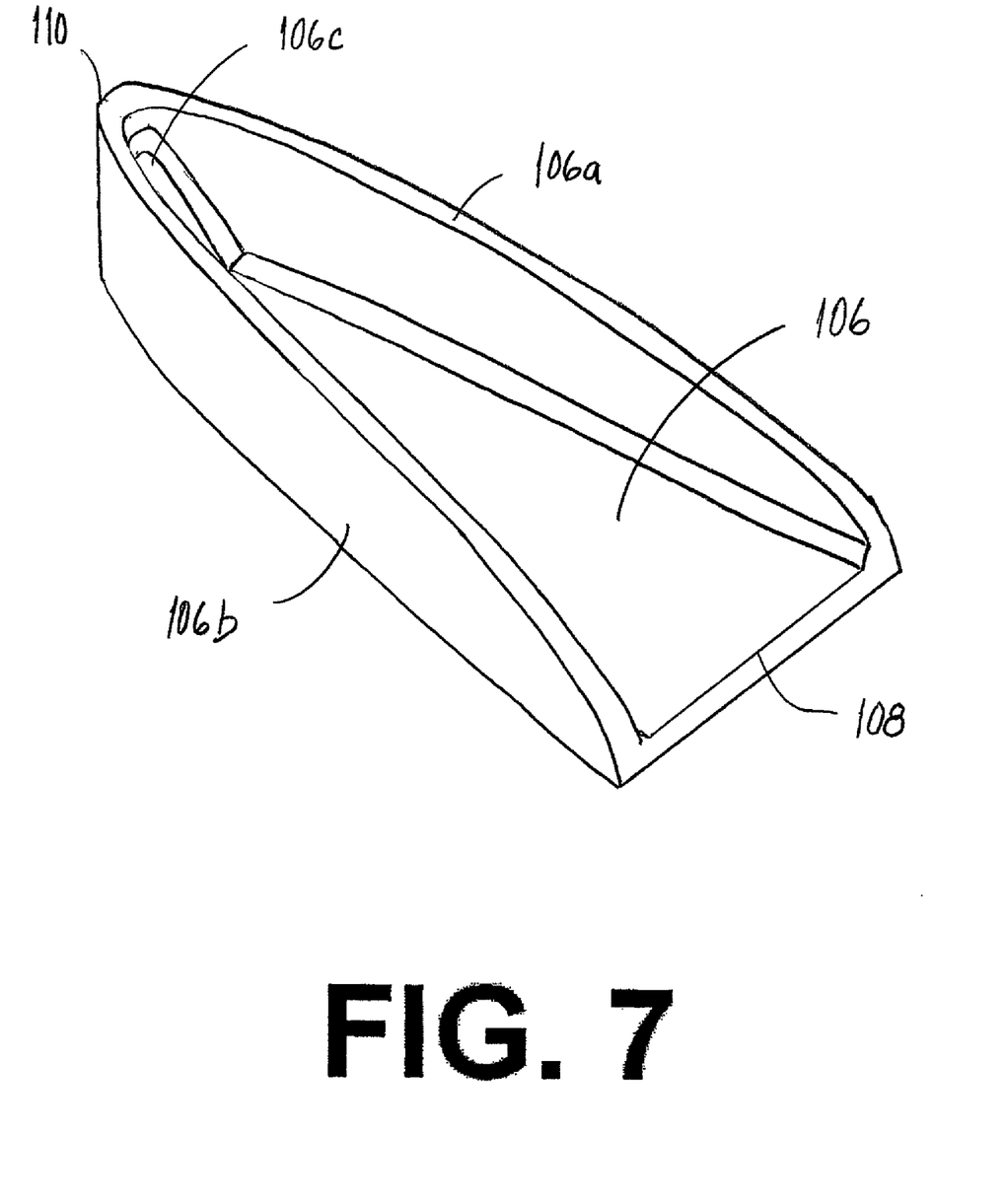
FIG. 7 is a perspective view of a channel according to an embodiment of the present invention.

FIG. 7 is a perspective view of the channel 106. The channel 106 is formed by sidewalls 106a, 106b. In a preferred embodiment, there is a draft angle between the walls 106a and 106b and the bottom of the channel 106. The draft angle provides for ease of molding the channel 106. As shown in this embodiment, sidewalls 106a, 106b meet at the second closed end 110 along a line 106c. Line 106c extends from the floor of channel 106 at an angle equal to or greater than about 90°. As mentioned above, other angles less than 90° will work to create a fountain but for ease of molding and manufacture an angle of at least 90° is preferable.

Figure 8:
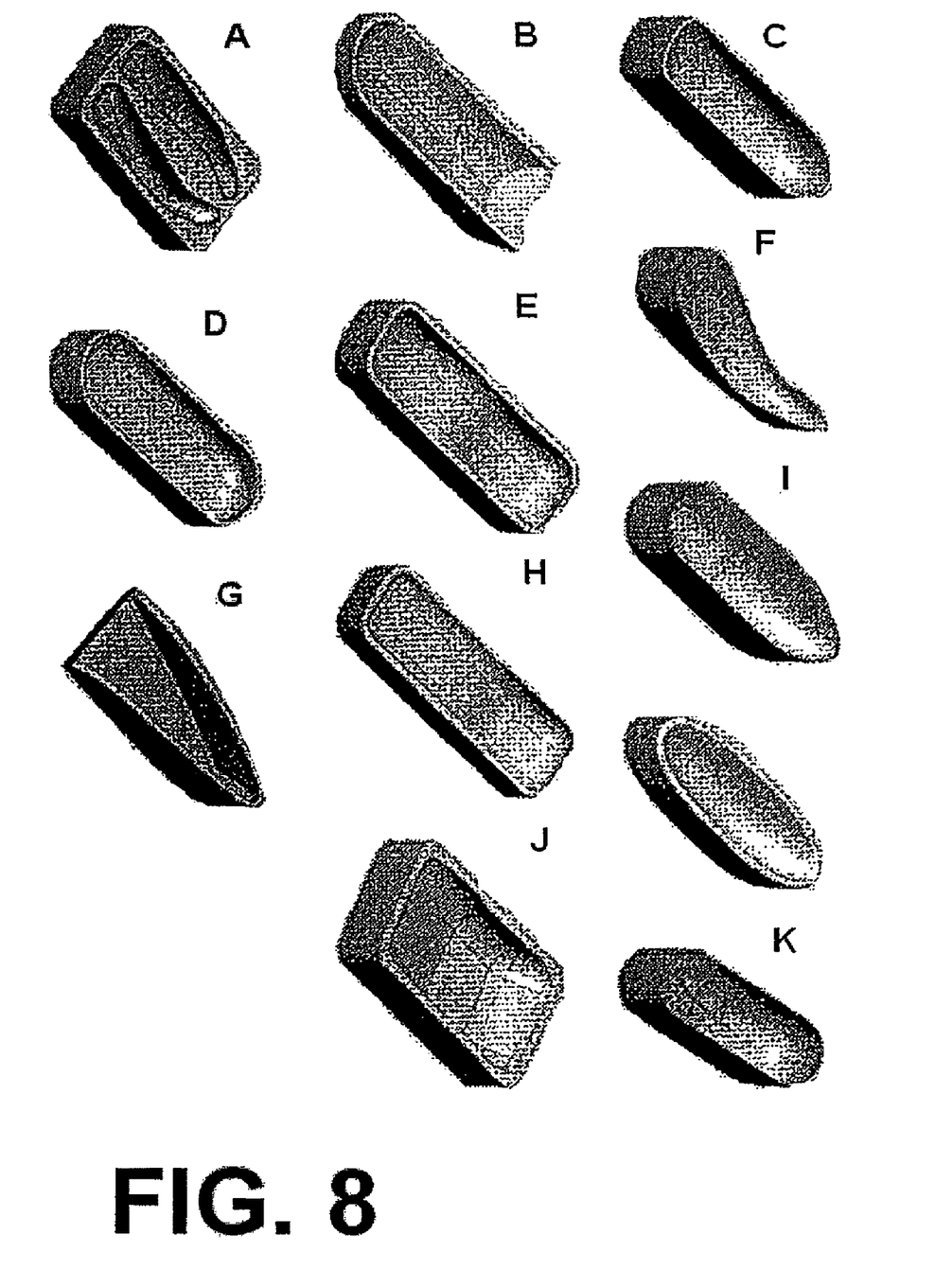

FIG. 8 depicts various alternative embodiments of channel 106. It should be noted that the unidirectional embodiments such as 8F and 8G are preferred. Further, both a flat bottom channel and trough bottom channels effectively provide the desired fountain.

Figure 9:
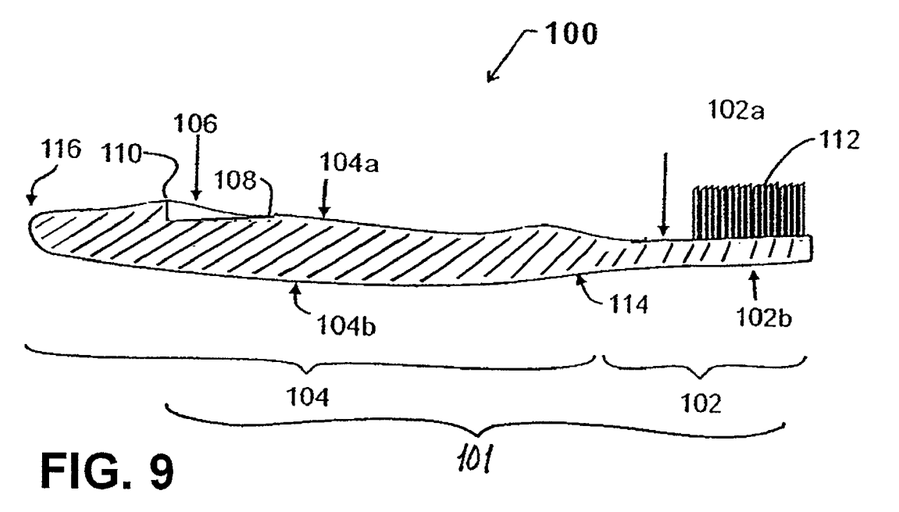
FIG. 9 is a sectional view of another embodiment of the toothbrush according to the present invention.
Figure 10:
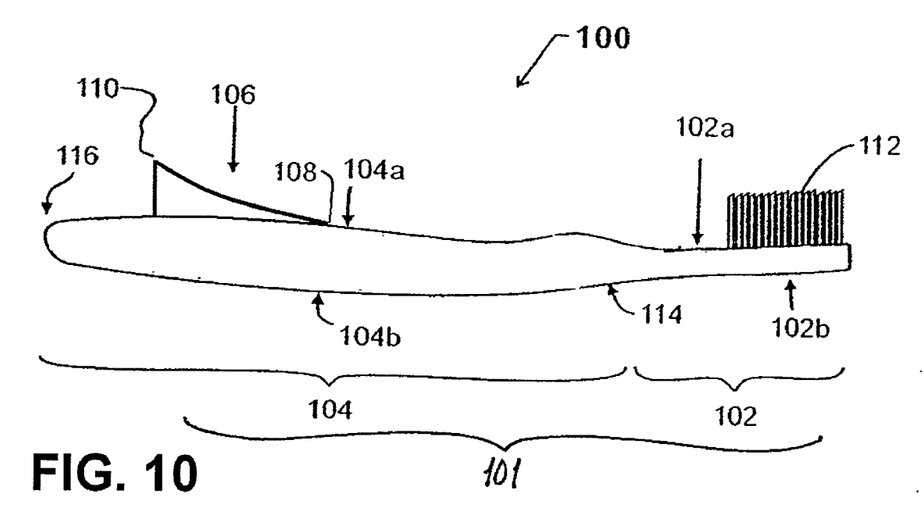
FIG. 10 is a sectional view of another embodiment of the toothbrush according to the present invention.

During brushing, it is possible that toothpaste and/or toothpaste suds may enter the channel 106. However the toothpaste and toothpaste suds are prevented from accumulating in the channel 106 because the user rinses the channel 106 each time the user orally rinses. Nonetheless, it may be desirable to prevent the entrance of toothpaste and/or toothpaste suds into the channel so that the fountain 120 includes only clean water. FIGS. 9 and 10 shows a further embodiment in which the first open end 108 and the second closed end 110 are arranged at a top 104a of the handle 104 to prevent toothpaste and/or toothpaste suds from entering the channel during brushing. As shown in FIG. 9, the channel 106 is formed integrally with the handle 104. Alternatively, as shown in FIG. 10, the channel 106 is affixed to the handle 104. It should be noted that during the molding of the handle 104, a cutout can be produced and an insert comprising channel 106 can then be inserted into the cutout. In alternative embodiments, the first open end 108 to the second closed end 110 can be arranged opposite the embodiments shown in FIGS. 9 and 10 such that the first open end 108 is arranged proximate to the end 116.

Figure 11:
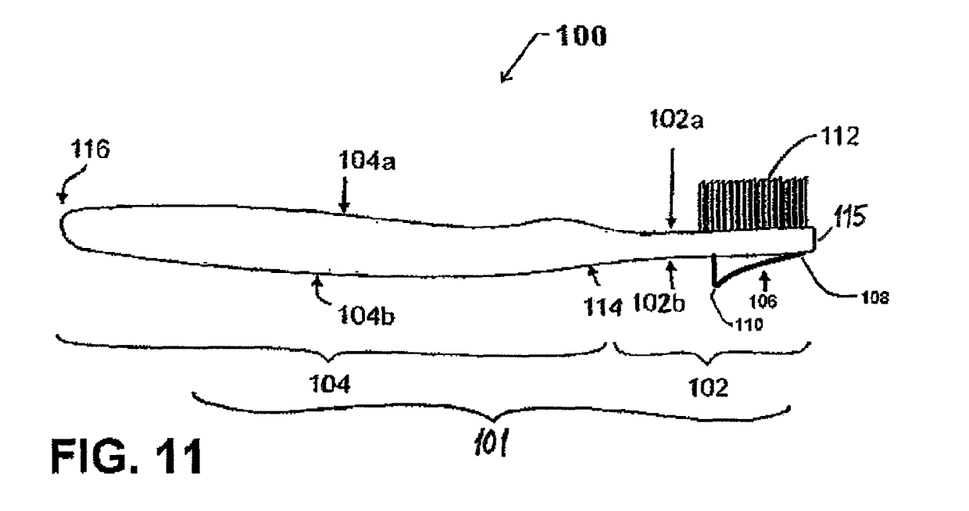
FIG. 11 is a side view of another embodiment of the toothbrush according to the present invention.

Although the channel 106 is arranged in the handle 104 of the toothbrush in the previous embodiments, the channel 106 may alternatively be affixed to the head 102 as shown in FIG. 11. This embodiment allows a user to merely flip the toothbrush 100 upside-down to use the channel 106 when the user is holding the toothbrush for brushing teeth. The first open end 108 and the second closed end 110 may be configured as in the previously described embodiments. For example, the flow out of the closed end 110 may be directed toward the head end 115, perpendicularly to the bottom 102b, or toward the handle 104. While FIG. 11 depicts the channel 106 extending from the surface 102b, it should be noted that the channel 106 can be molded into the surface 102b so that the surface 102b is substantially planar.

Instead of being arranged exclusively in the head 102 or in the handle 104, the channel 106 may extend from the head 102 to the handle 104. Furthermore, the channel 106 is depicted, for example, in FIGS. 1 and 9 as being substantially straight between the two ends 108, 110. However, the channel path and/or the side walls 106a, 106b may alternatively be formed as a curved section or an arc between the two ends or may include any combination of straight and curved sections as shown in FIG. 8. Further, whether integrally formed or affixed to one or more of the handle 104 and head 102, the channel 106 can be located anywhere along topside 102a, 104a or bottom side 102b, 104b of toothbrush 100. Alternatively, the channel 106 is located on a side of toothbrush 100 connecting top side 102a, 104a to bottom side 102b, 104b.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements, which perform substantially the same function in substantially the same way to achieve the same results, are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A toothbrush, comprising:
   a head portion having bristles projecting from said head portion;
   a body having a handle portion connected to the head portion, the body having a plurality of sides; and
   an open channel arranged on at least one of the head portion and the body portion, the open channel comprising:
   a first end open end;
   a second end closed end such that said first end is in communication with said second end through said open channel;

a pair of side walls between the first open end and the second closed end; and a channel floor delimited by the open end, the closed end, and the side walls, wherein the pair of side walls extend from the channel floor and a depth of the channel increases from the first open end to the closed second end, and wherein said first open end and said second closed end are arranged so that at least a portion of a substantially downward running stream of water directed into said first open end is redirected through said open channel and out of the second closed end to form a fountain, thereby availing to a user of the toothbrush a supply of water for rinsing.

2. The toothbrush of claim 1, wherein at least one of said first and second ends are arranged on said head portion.

3. The toothbrush of claim 2, wherein both of said first and second ends are arranged on said head portion on a side of said head portion opposite the bristles.

4. The toothbrush of claim 1, wherein said channel floor defines a bowl-shaped trough.

5. The toothbrush of claim 1, wherein a width of said first end between the pair of walls is between 2 mm and 14 mm.

6. The toothbrush of claim 5, wherein said width of said first end between the pair of walls is 4.5 mm.

7. The toothbrush of claim 6, wherein a height of the pair of side walls at the second end are each between about 2 mm and about 6 mm.

8. The toothbrush of claim 7, wherein the height of the pair of side walls at the second end is about 4.5 mm.

9. The toothbrush of claim 1, wherein said a channel floor between the open end and the closed end is at least 10 mm.

10. The toothbrush of claim 1, wherein the second closed end is substantially V-shaped.

11. The toothbrush of claim 1, wherein the second closed end is substantially U-shaped.

12. The toothbrush of claim 1, wherein the channel is integrally formed with at least one of the head portion and the body portion.

13. The toothbrush of claim 1, wherein the channel is affixed to at least one of the head portion and the body portion.

14. The toothbrush of claim 1, wherein each of the pair of side walls extend radially from the toothbrush and rise from the first open end to the second closed end at an angle.

15. The toothbrush of claim 1, wherein the pair of side walls are arranged symmetrically with respect to a longitudinal axis of the toothbrush.

16. The toothbrush of claim 1, wherein the side walls are arranged asymmetrically with respect to a longitudinal axis of the toothbrush.

17. A toothbrush of claim 1, wherein the closed end has a diameter of about at least about 2 mm in diameter.

18. The toothbrush of claim 1, wherein the channel is arranged to form the fountain directed away from the head portion of the toothbrush.

19. The toothbrush of claim 17, wherein the channel floor is substantially flat.

* * * * *